United States Patent [19]

Lavanish et al.

[11] 4,426,527

[45] Jan. 17, 1984

[54] 3-[5- OR 3-SUBSTITUTED-1,2,4-OXADIAZOL-3- OR -5-YL]-1-SUBSTITUTED-4-SUBSTITUTED-5-SUBSTITUTED OR UNSUBSTITUTED-2-IMIDAZOLIDINONES

[75] Inventors: Jerome M. Lavanish, Akron; Barry Van Gemert, Massillon, both of Ohio

[73] Assignee: PPG Industries, Inc., Pittsburgh, Pa.

[21] Appl. No.: 348,479

[22] Filed: Feb. 12, 1982

[51] Int. Cl.³ .................................. C07D 413/04
[52] U.S. Cl. .................................. 548/133; 71/92
[58] Field of Search .................................. 548/133

[56] References Cited

U.S. PATENT DOCUMENTS

| | | | |
|---|---|---|---|
| 4,021,439 | 5/1977 | Krenzer | 71/90 |
| 4,023,957 | 5/1977 | Krenzer | 71/90 |
| 4,028,375 | 6/1977 | Krenzer | 71/90 |
| 4,061,648 | 12/1977 | Krenzer | 71/90 |
| 4,063,924 | 12/1977 | Krenzer | 71/90 |
| 4,097,486 | 6/1978 | Krenzer | 71/90 |
| 4,243,409 | 1/1981 | Schmidt et al. | 71/92 |
| 4,268,679 | 5/1981 | Lavanish | 71/92 |
| 4,302,239 | 11/1981 | Lavanish | 71/88 |

*Primary Examiner*—Mary C. Lee
*Attorney, Agent, or Firm*—Edward J. Whitfield

[57] ABSTRACT

This invention concerns certain 3-[5- or 3-substituted-1,2,4-oxadiazol-3- or -5-yl]-1-substituted-4-substituted-5-substituted or unsubstituted-2-imidazolidinones having herbicidal activity and the use thereof to control weed growth.

3 Claims, No Drawings

3-[5- OR 3-SUBSTITUTED-1,2,4-OXADIAZOL-3- OR -5-YL]-1-SUBSTITUTED-4-SUBSTITUTED-5-SUBSTITUTED OR UNSUBSTITUTED-2-IMIDAZOLIDINONES

FIELD OF THE INVENTION

This invention concerns certain 3-[5- or 3-substituted-1,2,4-oxadiazol-3- or -5-yl]-1-substituted-4-substituted-5-substituted or unsubstituted-2-imidazolidinones having herbicidal activity and the use thereof to control weed growth.

DESCRIPTION OF THE INVENTION

This invention relates to herbicidally active 3-[5- or 3-substituted-1,2,4-oxadiazol-3- or -5-yl]-1-substituted-4-substituted-5-substituted or unsubstituted-2-imidazolidinones represented by the formula:

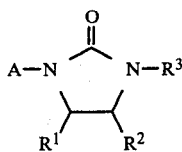

wherein:

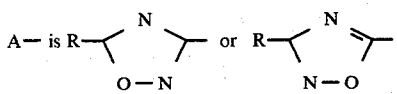

R is alkyl or haloalkyl of up to 6 carbon atoms, cycloalkyl of from 3 to 8 carbon atoms, alkenyl or alkynyl of up to 5 carbon atoms, $-R^4-O-R^5$ or $R^4-S-R^5$ wherein $R^4$ is alkylene of up to 6 carbon atoms and $R^5$ is alkyl of up to 6 carbon atoms,

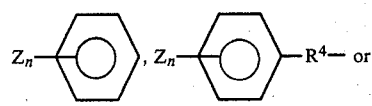

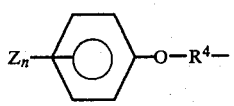

wherein Z is nitro, halogen, trifluoromethyl or $R^5$ and n is 0, 1, 2, or 3;

$R^1$ is hydroxy, halogen,

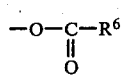

wherein $R^6$ is alkyl or haloalkyl of up to 6 carbon atoms, cycloalkyl of from 3 to 8 carbon atoms, alkenyl or alkynyl of up to 5 carbon atoms or

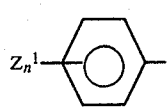

wherein $Z^1$ is nitro, halogen, trifluoromethyl, alkyl or alkoxy of up to 8 carbon atoms and n is 0, 1, 2 or 3 or

wherein $R^7$ and $R^8$ are the same or different and represent hydrogen, alkyl or haloalkyl of up to 6 carbon atoms; or $R^7$ can be

$R^2$ is hydrogen, hydroxy, alkyl, or haloalkyl of up to 4 carbon atoms or allyl; and $R^3$ is alkyl of up to 3 carbon atoms or allyl;

Some alkyl groups of which the various constituents in the above formula are representative are, for example, methyl, ethyl, n-propyl, isopropyl, n-butyl, isobutyl, sec-butyl, pentyl, hexyl, or the like, including combinations thereof, e.g., dimethylethyl. Exemplary alkoxy groups are methoxy, ethoxy, propoxy, butoxy, octoxy, and the like. As examples of cycloalkyl groups there may be mentioned cyclopropyl, cyclobutyl, cyclopentyl, cyclohexyl, cyclopentyl, and cyclooctyl. Allyl, butenyl, pentenyl, propynyl, butynyl, pentynyl and the like are exemplary of suitable alkenyl and alkynyl groups represented by the various constituents in the above formula. Representative suitable alkylene groups are, for example, methylene, ethylene, propylene, butylene, pentylene, or hexylene. As the halogen substituents, there may be mentioned chlorine, bromine, iodine, or fluorine, preferably chlorine or bromine.

Preferred compounds according to this invention are those wherein R and $R^3$ are alkyl, $R^1$ is hydroxy, $R^2$ is hydrogen or hydroxy and X is oxygen, some examples of which are 3-[5-(1,1-dimethylethyl)-1,2,4-oxadiazol-3-yl]-1-methyl-4-hydroxy-2-imidazolidinone, 3-[5-(1,1-dimethylethyl)-1,2,4-oxadiazol-3-yl]-1-methyl-4,5-dihydroxy-2-imidazolidinone and 3-[3-(1,1-dimethylethyl)-1,2,4-oxadiazol-5-yl]-1-methyl-4,5-dihydroxy-2-imidazolidinone. As exemplary of additional compounds believed to have herbicidal activity in accordance with this invention, there may be mentioned 3-[5-(1,1-dimethylethyl-1,2,4-oxadiazol-3-yl]-1-methyl-4-acetoxy-2-imidazolidinone, 3-[5-(1,1-dimethylethyl)-1,2,4-oxadiazol-3-yl]-1-methyl-4-benzoyloxy-2-imidazolidinone and 3-[5-(1,1-dimethylethyl)-1,2,4-oxadiazol-3-yl]-1-methyl-4-butyryloxy-2-imidazolidinone.

Compounds of this invention of the 3-yl series wherein $R^1$ is hydroxy and $R^2$ is other than hydroxy, e.g., hydrogen, may conveniently be prepared by reacting, in a first step, an appropriately substituted carbonyl chloride of the formula R—COCl, where R is as previously defined with cyanamide to prepare a compound of the formula R—CO—NHC≡N. This reaction is typically conducted in a cold, alkaline reaction medium the reaction product being crystallized by treatment of the reaction mixture with a cold, dilute aqueous acidic salt solution, e.g., dilute aqueous hydrochloric acid saturated with sodium chloride.

In a second step, the isolated reaction product from step one is reacted with hydroxylamine hydrochloride in the presence of an acid acceptor to prepare the corresponding 3-amino-5-(substituted)-1,2,4-oxadiazole of the formula:

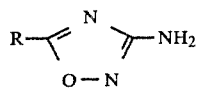

Compounds of the 5-yl series may be prepared by reaction of an appropriate nitrile of the formula R—C≡N where R is as previously defined, with an alcohol and hydrogen chloride, followed by reaction with cyanamide and then with hydroxylamine as described by K. R. Huffman and F. C. Schaefer, J. Org. Chem. 28, 1816 (1963) to give the corresponding 5-amino-3-(substituted)-1,2,4-oxadiazole of the formula:

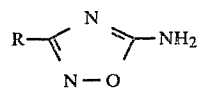

The isoxazolamine is then phosgenated to the corresponding isocyanate of the formula A—NCO wherein A is as previously defined. The isocyanate is then reacted in a third step, with an appropriately substituted amino acetaldehyde dialkyl acetal of the formula $R^3$—NH—CH($R^2$)CH($OR^9$)$_2$, wherein $R^2$ and $R^3$ are as previously defined and $R^9$ is alkyl of up to 6 carbon atoms or —CH($OR^9$) forms a 5 or 6 membered heterocyclic ring which may contain up to 3 hetero atoms to form an acetal urea of the formula:

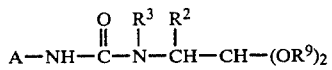

In the final step the acetal urea is hydrolyzed by heating in a dilute aqueous acid medium, e.g., hydrochloric acid, to form a compound of the invention wherein $R^1$ is hydroxy.

If it is desired to prepare a compound of the invention wherein both $R^1$ and $R^2$ are hydroxy a 3- or 5-amino-3- or 5-(substituted)-1,2,4 oxadiazol (prepared as described previously) is reacted with an appropriately substituted isocyanate of the formula $R^3$—N=C=O, wherein $R^3$ is as previously defined to form a urea of the formula A—N(H)—C(O)—N($R^3$)—H which is reacted with glyoxal to form a compound of the invention having a hydroxy substituent in both the $R^1$ and $R^2$ positions.

A compound of the invention wherein $R^1$ is halogen, e.g., chlorine or bromine, may be prepared by reacting a compound of the invention of the formula:

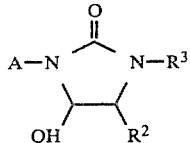

wherein A, $R^2$ and $R^3$ are as previously defined with a suitable halogenating agent typically in the presence of an inert solvent and optionally in the presence of an acid binding agent. When it is is desired to halogenate compounds of the invention wherein both $R^1$ and $R^2$ are hydroxy, it is necessary to protect the hydroxy group at the $R^2$ position by, for example, alkylation followed by removal of the alkyl group subsequent to halogenation.

To prepare a compound of the invention wherein $R^1$ is

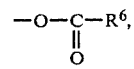

a compound of the invention having the formula:

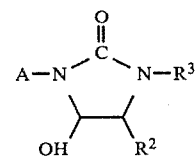

is reacted with an anhydride of the formula:

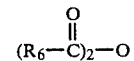

wherein A, $R^2$, $R^3$ and $R^6$ are as previously defined. This reaction is typically conducted at reflux temperature in the presence of an acid acceptor such as triethylamine, pyridine, N,N-dimethylaniline or the like and in the presence of an inert solvent such as benzene, methylene chloride, chloroform, ethyl acetate, tetrahydrofuran or the like.

It is of course to be realized that all of the above described modes of preparation employ well-known analytic techniques and that any compound within the scope of the invention may readily be prepared by one skilled in the art using the same or similar methods. Synthesis of a specific compound within the scope of this invention is illustrated by the following Example:

EXAMPLE I

Preparation of 3-[5-(1,1-dimethylethyl)-1,2,4-oxadiazol-3-yl]-1-methyl-4-hydroxy-2-imidazolidinone (a) To a flask provided with a magnetic stirrer was charged 160 milliliters of 10 percent aqueous sodium hydroxide and 34 grams of a 50 percent aqueous cyanamide solution. The flask contents were maintained at a temperature in the range of 0° to 5° C. by immersion in a salt and ice bath. To the cold solution was added dropwise, with constant stirring, 50 milliliters (0.4 mole) of trimethylacetyl chloride. After addition of about 0.2 mole of trimethylacetyl chloride, sufficient additional aqueous sodium hydroxide solution was added to maintain a pH of about 10. The reaction mixture was stirred in the ice bath for one-half hour, after which the ice bath was removed and stirring was continued for an additional one-half hour. Cold dilute aqueous hydrochloric acid saturated with sodium chloride was then added until the mixture turned milky and crystal formation was observed. The crystalline material was separated by filtration, suction dried and dried in a vacuum oven yielding about 40 grams of dried material.

(b) The crystalline material prepared in paragraph (a) of this Example was added incrementally, with stirring, to a mixture of 25 grams of hydroxylamine hydrochloride in 125 milliliters of pyridine, the temperature of the reaction mixture being maintained below 40° C. A mild exotherm was observed. After addition was complete, the reaction mixture was stirred over the weekend at ambient temperature. The reaction mixture was then diluted with 100 milliliters of water and 100 milliliters of 30 percent aqueous sodium hydroxide, the latter added in four increments. After phase separation, the organic layer was removed and concentrated on a rotary evaporator to remove pyridine leaving an oily residue which crystallized upon addition of saturated aqueous sodium chloride. A total of 24.77 grams of crystals melting at 81° to 83° C. were obtained.

(c) To a 500 milliliter flask provided with a paddle stirrer, a gas inlet tube, and a dry ice condenser fitted with a drying tube was charged 20 grams of the crystalline material prepared in paragraph (b) of this Example dissolved in 400 milliliters of toluene. Dry hydrogen chloride gas was added resulting in the formation of a voluminous precipitate after which phosgene was bubbled in below the liquid surface resulting in dissolution of most of the precipitate. The reaction mixture was stirred overnight at ambient temperature and then gently warmed to remove excess phosgene. Considerable frothing was observed until the temperature reached about 70° C. The flask was then purged with nitrogen at a temperature of 70° to 80° C. for about 8 hours after which heating was discontinued and nitrogen purging continued overnight. The mixture was stripped on a rotary evaporator to remove toluene leaving a white-yellow solid. The solid was placed in a vacuum oven at moderate heat. When sublimation of the solid was noted, the solid was removed from the oven, 20 grams of solid material being obtained.

(d) To a flask provided with reflux condenser and a magnetic stirring bar was charged 3.14 grams of the solid material prepared as described in paragraph (c) of this Example dissolved in 75 milliliters of toluene and 2.4 grams of methylamino acetaldehyde dimethylacetal. The mixture was stirred for one hour at ambient temperature and then slowly heated to just below reflux temperature and maintained at this temperature, with stirring, overnight. The mixture was then cooled, filtered and stripped on a rotary evaporator to remove toluene leaving an oily residue. The oil residue was then stirred vigorously with 75 milliliters of water containing 0.75 milliliter of concentrated sulfuric acid. The mixture was then gradually heated, with stirring, to 80° C. and maintained at this temperature for one-half hour, most of the oil going into solution. The reaction mixture was then filtered to remove undissolved oil and the clear aqueous solution was extracted with two 75-milliliter portions of chloroform. The combined chloroform extracts were concentrated on a rotary evaporator leaving an oily residue which crystallized upon cooling and addition of a small amount of diethyl ether. After filtration and washing with diethyl ether, 1.5 grams of crystalline product were obtained melting at 125° to 129° C., and identified by mass spectrum and NMR analyses as 3-[5-(1,1-dimethylethyl)-1,2,4-oxadiazol-3-yl]-1-methyl-4-hydroxy-2-imidazolidinone.

The mode of synthesis of a specific compound of this invention has been illustrated by the foregoing Example; but it is to be understood that any compound contemplated within the scope of this invention may be prepared by those skilled in the art simply by varying the choice of starting materials and using the illustrated techniques or other suitable techniques.

The compounds of this invention are believed effective in regulating the growth of a variety of undesirable plants, i.e., weeds, when applied, in an herbicidally effective amount, to the growth medium prior to emergence of the weeds or to the weeds subsequent to emergence from the growth medium. The term "herbicidally effective amount" is that amount of compound or mixture of compounds required to so injure or damage weeds such that the weeds are incapable of recovering following application. The quantity of a particular compound or mixture of compounds applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as 0.2 or less pound per acre to 10 or more pounds per acre of compound or mixtures of compounds may be required. Of course, the efficacy of a particular compound against a particular weed species may readily be determined by relatively straightforward laboratory or field testing in a manner well known to the art.

The compounds of this invention may be used as such or in formulation with agronomically acceptable adjuvants, inert carriers, other herbicides, or other commonly used agricultural compounds, for example, pesticides, stabilizers, safeners, fertilizers, and the like. The compounds of this invention, whether or not in formulation with other agronomically acceptable materials, are typically applied in the form of dusts, granules, wettable powders, solutions, suspension, serosols, emulsions, dispersions or the like in a manner well known to the art. When formulated with other typically used agronomically acceptable materials, the amount of compound or compounds of this invention present in the formulation may vary over a wide range, for example, from about 0.05 to about 95 percent by weight on weight of formulation. Typically such formulations will contain from about 5 to about 75 percent by weight of compound or compounds of this invention.

The compounds of this invention, as exemplified by the compound prepared in Example I have been found effective in controlling a variety of broadleaf and grassy weeds when applied either preemergence or postemergence. The compound prepared according to Example I was tested for herbicidal activity against various weed species planted in flats under controlled laboratory conditions of light, temperature, and humidity, using techniques known to the art. In preemergence evaluation, a solvent solution of the test compound is applied at the desired rate to the weed species prior to emergence from the growth medium whereas in postemergent evaluation a solvent solution of the test compound is applied at the desired rate directly on the growing plant, the toxic effect of the compound being determined by visual inspection periodically after application.

The test compound effectiveness is evaluated against a control flat planted with the same weed species undergoing test to which control flat is added an equivalent amount of carrier solvent as that applied to the test flats. The herbicidal effectiveness of the test compound on a given weed species is evaluated by visual inspection and by assigning a Numerical Injury Rating on a Scale of From 0 (no injury) to 10 (all weeds dead). The Numerical Injury Rating is a quantitative measure of the percentage of injury to a particular weed species and is the primary measure of the herbicidal effectiveness of a test compound.

The following Table sets forth Numerical Injury Ratings of the compound prepared in Example 1 against a variety of common weed species at application rates of 10 pounds per acre preemergence and 10 pounds per acre postemergence. The Numerical Injury Ratings were determined twenty one days subsequent to application.

| Weed | Pre | Post |
|---|---|---|
| Teaweed | 10 | 10 |
| Jimsonweed | 10 | 10 |
| Wild Mustard | 10 | 10 |
| Coffeeweed | 9 | 10 |
| Velvetleaf | 10 | 10 |
| Tall Morningglory | 9 | 9 |
| Yellow Nutsedge | 4 | 10 |
| Yellow Foxtail | 10 | 10 |
| Large Crabgrass | 9 | — |
| Johnsongrass | 10 | 6 |
| Wild Oats | 10 | 10 |
| Barnyardgrass | 10 | 9 |

Although the invention has been described with specific references and specific details of embodiments thereof, it is to be understood that it is not intended to be so limited since changes and alterations therein may be made by those skilled in the art which are within the full intended scope of this invention as defined by the appended claims.

What is claimed is:

1. A compound represented by the formula:

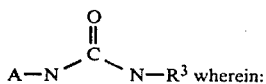

wherein:

A— is 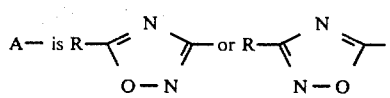

R is alkyl or haloalkyl of up to 6 carbon atoms, cycloalkyl of from 3 to 8 carbon atoms, alkenyl or alkynyl of up to 5 carbon atoms, —R$^4$—O—R$^5$ or R$^4$—S—R$^5$ wherein R$^4$ is alkylene of up to 6 carbon atoms and R$^5$ is alkyl of up to 6 carbon atoms,

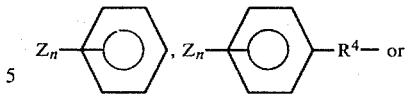

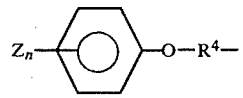

wherein Z is nitro, halogen, trifluoromethyl or R$^5$ and n is 0, 1, 2, or 3;

R$^1$ is hydroxy, halogen,

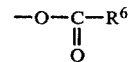

wherein R$^6$ is alkyl or haloalkyl of up to 6 carbon atoms, cycloalkyl of from 3 to 8 carbon atoms, alkenyl or alkynyl of up to 5 carbon atoms or

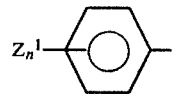

wherein Z$^1$ is nitro, halogen, trifluoromethyl, alkyl or alkoxy of up to 8 carbon atoms, and n is 0, 1, 2 or 3 or

wherein
R$^7$ and R$^8$ are the same or different and represent hydrogen, alkyl or haloalkyl of up to 6 carbon atoms; or R$^7$ can be

R$^2$ is hydrogen, hydroxy, alkyl, or haloalkyl of up to 4 carbon atoms or allyl; and
R$^3$ is alkyl of up to 3 carbon atoms or allyl.

2. The compound of claim 1 wherein R and R$^3$ are alkyl, R$^1$ is hydroxy and R$^2$ is hydrogen or hydroxy.

3. A compound of claim 2 which is 3-[5-(1,1-dimethylethyl)-1,2,4-oxadiazol-3-yl]-1-methyl-4-hydroxy-2-imidazolidinone.

* * * * *